United States Patent [19]

Inamoto et al.

[11] Patent Number: 6,008,189
[45] Date of Patent: Dec. 28, 1999

[54] INTRAVAGINAL PREPARATION CONTAINING PHYSIOLOGICALLY ACTIVE PEPTIDE

[75] Inventors: Shigeyuki Inamoto; Masaaki Uchida; Yukiko Inamoto, all of Kagawa-ken, Japan

[73] Assignee: Teikoku Seiyaku Kabushiki Kaisha, Kagawa-ken, Japan

[21] Appl. No.: 09/009,734

[22] Filed: Jan. 21, 1998

Related U.S. Application Data

[62] Division of application No. 08/557,104, filed as application No. PCT/JP94/00894, Jun. 2, 1994.

[30] Foreign Application Priority Data

Jun. 7, 1993 [JP] Japan ..................... 5-135738

[51] Int. Cl.$^6$ ............... A61K 9/02; A61K 38/00; A61K 47/12; A61K 47/14
[52] U.S. Cl. ............... 514/2; 424/433; 514/784; 514/785; 514/967
[58] Field of Search ............... 514/2, 3, 4.8, 12, 514/21.808, 967, 784, 785; 424/430, 433, 434, 436; 530/303, 307, 324

[56] References Cited

U.S. PATENT DOCUMENTS 5,482,706  1/1996  Igari et al. ............... 424/85.7
5,776,886  7/1998  Inamoto et al. ............... 514/2

FOREIGN PATENT DOCUMENTS 517211  12/1992  European Pat. Off. .

OTHER PUBLICATIONS

Remington's Pharmaceutical Sciences, 18th Ed., pp. 245–246 (1990).

*Primary Examiner*—Jeffrey E. Russel
*Attorney, Agent, or Firm*—Birch, Stewart, Kolasch & Birch, LLP

[57] ABSTRACT

The present invention relates to an improved intravaginal preparation containing a physiologically active peptide, which comprises a physiologically active peptide, a sucrose fatty acid ester and an organic acid with a pharmaceutically acceptable carrier or diluent, by which the physiologically active peptide can be absorbed safely and efficiently.

2 Claims, No Drawings

INTRAVAGINAL PREPARATION CONTAINING PHYSIOLOGICALLY ACTIVE PEPTIDE

This application is divisional of application Ser. No. 08/557,104, filed on Dec. 6, 1995, now U.S. Pat. No. 5,776,886. Application Ser. No. 08/557,104 is the national phase of PCT International Application No. PCT/JP94/00894 filed on Jun. 2, 1994 under 35 U.S.C. § 371. The entire contents of each of the above identified applications are hereby incorporated by reference.

TECHNICAL FIELD

This invention relates to an intravaginal preparation containing a physiologically active peptide. More particularly, it relates to an improved intravaginal preparation comprising a physiologically active peptide and as an absorption promoter a combination of a sucrose fatty acid ester and an organic acid, by which the active peptide can be effectively absorbed via vaginal mucous membrane with safety to human body.

PRIOR ART

The study on physiologically active peptides has recently been developed and benefitted by the recent significant development of science. The results of the fundamental studies include production of highly pure peptides on a large scale, clarification of the mechanism of the pharmacological activities including clarification of the structure of the drug-receptor in the therapy with the peptides, creation or improvement of animals useful as a model for studying diseases and thereby finding of new physiological activities, which are owing to the development of genetic engineering technique and purification technique. With such development, the physiologically active peptides are expected to be useful as a very important medicament in therapy of various diseases in the future, and nowadays, intensive studies have been done in order to use them clinically.

The representative peptides which have already been clinically used are insulin and calcitonin. The main diseases in which these peptides participate are diabetes and osteoporosis. It is considered that these diseases become significant by increase in population of old ages and are owing to the unbalanced diet resulting from the recent easy and rich dietary life, and population of patients suffering from such diseases has been increased, which is one of the social problems.

Insulin participates in permeation through membrane of saccharide, amino acids and potassium ion in muscles and the liver, activation of glycogen synthetic enzyme ribosome, promotion of synthesis of proteins and fatty acids, promotion of utilization of saccharides and inhibition of new production thereof, promotion of membrane permeability of saccharides in the fatty tissues, and promotion of synthesis of fatty acids, and it has clinically been used in the therapy of insulin-dependent diabetes and in the shock therapy of schizophrenia.

It is known that calcitonin participates in calcium metabolic homeostasis which is important to biobody, and it has clinically been used in the therapy of pain of osteoporosis in aged persons, especially in aged females, hypercalcemia and Paget's disease of bone. It has also been found that calcitonins participate in locomotorium disorder, diseases of digestive organs, endocrinic pathobolism, blood dyscrasias, cardiovascular disease, and the like, and hence it has been studied as to the possibility to use as a medicament in the therapy of various diseases.

However, these peptides are water-soluble high molecular compounds which are easily decomposed by gastric juice or proteases such as pepsin and trypsin, and hence, when they are administered by oral route, they are hardly absorbed arid cannot exhibit their activities. In order to exhibit their pharmacological activities, they are usually administered by injection. According to the administration method, the peptide preparation must be administered regularly and frequently for the therapy of the above chronic diseases, which disadvantageously forces the patient frequent attendance to hospitals. Moreover, injection causes pain at the injection site and psychic pain. Besides, injection possibly causes topical allergic reaction or muscular contracture to the patients. Accordingly, it has been desired to find an improved preparation which can easily be administered by the patients themselves.

It has been studied how to administer the peptides by other means than injection, for example, intrarectal, intranasal, oral, or intravaginal administration. It has been found that when the peptides are administered through mucous membrane, they are usually not absorbed alone, but the absorption thereof is promoted by administering together with a surface active substance or the like. Thus, there are many reports as to absorption promoters for peptides.

For example, Hirai et al. U.S. Pat. No. 4,659,696 and Uda et al. U.S. Pat. No. 4,670,419 disclose intranasal, intravaginal or intrarectal preparations comprising cyclodextrin and a hydrophilic medicament which is hardly absorbed in the gastric and intestinal tracts. The medicaments contained in the preparations of the above literatures include peptides such as insulin, LH-RH analogues, oxytocin and TRH.

Morishita et al. U.S. Pat. No. 4,609,640 discloses intrarectal or intravaginal preparations having excellent absorbability of a medicament which comprise a water-soluble medicament and a specific water-soluble chelating agent. The medicaments inclusive in the preparations include peptides having hormone activities such as insulin, somatostatin, and calcitonin.

European Patent Publication No. 0183527 discloses an intranasal calcitonin preparation having high absorbability of the medicament which comprises calcitonin and at least one absorption promotor selected from the group consisting of benzilic acid or its salts, capric acid or its salts, polyethylene glycol 400, pyridoxal or its salts, malic acid or its salts, and pyrophosphoric acid or its salts. It is disclosed therein that the absorption of the medicament through nasal mucous membrane is improved by using one of the specific absorption promoters.

British Patent Publication No. 2,127,689 discloses an intranasal pharmaceutical preparation comprising calcitonin incorporated into a suitable liquid carrier or diluent for administration through nasal cavity mucous membrane, benzalkonium chloride and/or a surfactant being suitable for intranasal administration. When the pharmaceutical preparation contains a surfactant, the surfactant is preferably a nonionic surfactant, most preferably polyoxyalkylene higher alcohol ether. It is mentioned therein that the calcitonin-containing intranasal pharmaceutical preparation has improved bioavailability and good stability.

Morimoto et al. (J. Pharm. Pharmacol., 1985, 37, 759–760) disclose the effects of a nonionic surfactant, polyoxyethylene sorbitan monooleate and polyoxyethylene-9-lauryl ether on the intrarectal absorption of a semi-synthetic analogue of eel calcitonin and also the absorption promoting effects of a polyacrylic acid gel base. It has been found that the polyacrylic acid gel base improves the absorption of insulin through the rectal, vaginal and nasal mucous membranes, and the absorption of calcitonin through the rectal and nasal mucous membranes.

According to the first study, there have been used as an absorption promoter amphoteric and cationic surfactants and particularly a nonionic surfactant, polyoxyethylene lauryl ether, but the preferable ether-type surfactant destroys nasal mucous membrane and thereby promotes the absorption of a medicament. Moreover, according to the first report, it is mentioned that when a medicament having less absorbability is administered together with an enamine, a carboxylic acid and a surfactant, the absorption of the medicament is enhanced.

On the other hand, Nakata et al. Japanese Patent First Publication (Kokai) No. 10020/1987 discloses pharmaceutical preparations such as troches, buccal preparations, sublingual tablets, chewable tablets, dropping formulation, water-soluble gel preparations, and adhesions applied to oral mucous membrane, which comprise calcitonin and a sucrose fatty acid ester having an HLB value in the range of 11–16.

However, even by the above-mentioned various studies, the preparations are still not satisfactory in view of less absorption and topical irritation. Thus, there has still been sought an improved preparation having higher safety and higher absorbability of the active ingredient under taking into account the physiological and histological differences in age, sex, etc. of patients.

The present inventors have already provided in Japanese Patent First Publication (Kokai) Nos. 294632/1989 and 99021/1991 intravaginal preparations which contain as an absorption promotor one or more substances selected from N-acylamino acids, cholic acids, pectic acid, taurine, saccharin, glycyrrhizic acid, aspartame, and their salts, alkylphenyl ethers, anionic surfactants, nonionic surfactants, medium chain aliphatic carboxylic acids or their salts.

It is well known that the secretion of hormones has changed in postmenopausal females, and their vaginas are also different in the physiological and histological circumstances and structure, such as pH value and thickness of mucous membrane within the vagina. Thus, when applying intravaginal preparations to postmenopausal females, it is necessary to consider the above various conditions. The above-mentioned preparation by the present inventors has been prepared under taking into account these various factors, but it is still necessary to improve more in order to apply to the postmenopausal females.

DISCLOSURE OF THE INVENTION

Under taking into account the above-mentioned various factors, the present inventors have further intensively studied to find an improved preparation in order to solve the above-mentioned problems, and have now found during the development of a preparation suitable for administration of a physiologically active peptide by other means than injection that an intravaginal preparation containing an organic acid alone or an intravaginal preparation containing a sucrose fatty acid ester alone can show an improved absorption of the active ingredient, but when both of them are incorporated into the intravaginal preparation, it shows far excellent absorbability of the active ingredient, and have accomplished the present invention. Thus, the present invention provides an improved intravaginal preparation having high absorbability of the active ingredient which comprises a physiologically active peptide and at least a sucrose fatty acid ester and an organic acid or a pharmaceutically acceptable salt thereof.

BEST MODE FOR CARRYING OUT THE INVENTION

The physiologically active peptide used in the present invention includes peptides having a molecular weight of less than 15,000. Suitable examples of the peptide are insulin, angiotensin, vasopressin, desmopressin, LH-RH (luteinizing hormone-releasing hormone), somatostatin, calcitonin, glucagon, oxytocin, gastrins, somatomedins, secretin, h-ANP (human atrial natriuretic polypeptide), ACTH (adrenocorticotropic hormone), MSH (melanocyte stimulating hormone), β-endorphin, muramyl-dipeptide, enkephalin, neurotensin, bombesin, VIP (vasoactive intestinal polypeptide), CCK-8 (cholecystokinin-8), PTH (parathyroid hormone), CGRP (calcitonin gene relating polypeptide), TRH (thyrotropin-releasing hormone), TSH (thyroid stimulating hormone), endothelin, TSH (thyroid stimulating hormone), and their derivatives.

The various peptides used in the present invention include not only naturally occurring peptides but also physiologically and pharmaceutically active synthetic and semi-synthetic derivatives or analogues thereof. For example, calcitonin used in the present invention includes not only natural calcitonins such as salmon calcitonin, human calcitonin, porcine calcitonin, eel calcitonin, chicken calcitonin, but also analogues such as $(Asu^{1.7})$-eel calcitonin, i.e. elcatonin. The most preferable peptide used in the present invention is calcitonin and PTH.

The amount of the physiologically active peptide contained in the intravaginal preparation of the present invention varies according to the kind of the peptide to be used, but it should be an effective amount for exhibiting the desired pharmacological activity thereof. For example, when calcitonin is used, it should be contained in an effective amount for the therapy of morbid conditions of diseases such as Paget's disease, hypercalcemia and osteoporosis. When PHT, CGRP, somatomedin or an analogue thereof is used, it is used in an effective amount for the therapy of bone metabolic disorders. When insulin is used, it is used in an effective amount for regulating the glucose level in blood, and treating diabetes. The effective amount of the other physiologically active peptides used in the present invention is also determined likewise.

The sucrose fatty acid ester used in the present invention includes an ester of sucrose with one or more fatty acids, for example, esters including from monoesters consisting of a molecule of sucrose and a molecule of fatty acid to octaesters consisting of a molecule of sucrose and eight molecules of fatty acid, and it is usually used in the form of a mixture of these esters. The sucrose fatty acid ester is generally referred to as sugar ester and is widely used an extremely safe additive in food, cosmetics and medicines. The fatty acid of the sucrose fatty acid ester includes, stearic acid, palmitic acid, lauric acid, oleic acid, and the like. Suitable examples of the sucrose fatty acid ester are sucrose stearic acid ester, sucrose palmitic acid ester, sucrose oleic acid ester, sucrose lauric acid ester, sucrose behenic acid ester, and sucrose erucic acid ester, and among them, sucrose stearic acid ester, sucrose palmitic acid ester, sucrose oleic acid ester and sucrose lauric acid ester are more preferable. One or more these esters are used in the present invention. The sucrose fatty acid ester is contained in an amount of 0.1 to 30 w/w %, preferably in an amount of 0.5 to 15 w/w % to the total weight of the preparation.

The organic acid used in the present invention is selected from the group consisting of a saturated aliphatic carboxylic acid having 2 to 6 carbon atoms, an unsaturated aliphatic carboxylic acid, an aromatic carboxylic acid, ascorbic acids, and a pharmaceutically acceptable salt thereof. The saturated aliphatic carboxylic acid includes a monobasic acid, a hydroxycarboxylic acid and a polycarboxylic acid. Suitable examples of the monobasic acid are acetic acid, propionic acid, butyric acid, valeric acid, capric acid, etc. Suitable examples of the hydroxycarboxylic acid are malic acid, lactic acid, tartaric acid, citric acid, etc. Suitable examples of the polycarboxylic acid are malic acid, succinic acid, tartaric acid, citric acid, fumaric acid, malonic acid, glutaric acid, adipic acid, etc. Suitable examples of the unsaturated aliphatic carboxylic acid are fumaric acid, maleic acid, etc. Suitable examples of the aromatic carboxylic acid are benzoic acid, phthalic acid, etc. The ascorbic acids are ascorbic acid, isoascorbic acid, etc. Among these organic acids, citric acid, tartaric acid, malic acid, lactic acid, succinic acid and benzoic acid are more preferable. One or more these organic acids are used in the present invention. The organic acid is contained in an amount of 0.1 to 20 w/w %, preferably in an amount of 0.5 to 10 w/w % to the total weight of the preparation.

These organic acids were found from natural plants and animals, like citric acid, tartaric acid, malic acid, lactic acid, and are widely distributed into natural resources, and are adopted routinely as food and drinks. The safety of these organic acids has been established as actual proof from ancient times. Besides, these organic acids have been also used as an additive in the pharmaceutical compositions.

As mentioned above, since the safety of the sucrose fatty acid ester and the organic acid used in the present invention has undoubtedly been established, the intravaginal preparation of the present invention can be a pharmaceutical preparation with an extremely high safety.

The intravaginal preparation of the present invention may optionally contain an animal protein and/or vegetable protein, which is/are not an essential component of the present preparation, but in order to prevent the active peptide from enzymatic-decomposition which may occur during the absorption procedure of the peptide after administration of the preparation, and/or in case that an unstable active peptide or a derivative thereof is used as an active ingredient, or in case that an active peptide is adsorbed at the wall of the vessel used in the mixing procedure of the components, if necessary. Such animal protein and vegetable protein are preferably ones conventionally used in food, cosmetics, or pharmaceutical compositions.

The animal protein includes albumin (e.g. bovine serum albumin, human serum albumin, etc.), lecithin, casein, gelatin, etc. The vegetable protein includes gluten, zein, soybean protein, lecithin, etc. The animal protein and the vegetable protein can be used alone or can be used together in the form of a combination thereof of an appropriate ratio.

The amount of the animal protein and/or the vegetable protein in the present intravaginal preparation varies according to the kind of the peptide to be stabilized by them, but it is in the range of 0.001 to 25 w/w % to the total weight of the preparation.

The preparation form of the present intravaginal preparation may be liquid preparations, gel preparations (gel preparation having high viscosity is more preferably), suppositories, films, tablets, soft capsules, tampons, creams, etc., all comprising a physiologically active peptide, an organic acid, a sucrose fatty acid ester, and if necessary, an animal protein and/or vegetable protein.

The present intravaginal preparation may be prepared by mixing directly a physiologically active peptide, an organic acid and a sucrose fatty acid ester, and if necessary, an animal protein and/or vegetable protein, or dissolving or mixing them in purified water or physiological saline solution, and then, followed by mixing the resulting solution or mixture with a conventional base for intravaginal preparation in a conventional manner.

The pH value of the present intravaginal preparation is preferably a pH value closest to that of the vagina. After dissolving an organic acid in a diluent where said diluent is used in an amount as small as possible but necessary for dissolving the organic acid, the pH value of the organic acid solution is adjusted to 3 to 7, preferably 3 to 5 by adding a basic compound into said organic acid solution. The basic compound used for adjusting the pH value may be a conventional one but the resulting final solution should be non-toxic and non-irritative to humans. Suitable examples of the basic compound are bases such as sodium hydroxide, potassium hydroxide, calcium hydroxide, etc. Subsequently, a physiologically active peptide, a sucrose fatty acid ester, and if necessary, an animal protein and/or vegetable protein are added into said organic acid solution and dissolved or mixed.

The gel preparation having high viscosity may be prepared by adding a conventional thickening agent into the above solution, if necessary, and suitable examples of the thickening agent are cellulose lower alcohol ether, PVA (polyvinyl alcohol), PVP (polyvinylpyrrolidone), polyoxyethyleneoxy-propylene glycol block copolymer (PLURONIC™), etc.

The present intravaginal preparation may contain one or more additives such as vehicles, isotonic agents, preservatives, antioxidants and coloring agents. For example, vehicles (e.g. starch, dextrin, D-mannitol, cyclodextrin, tragacanth, etc.); isotonic agents (e.g. sodium chloride, potassium chloride, sodium carbonate, etc.); benzoic acid and p-hydroxy-benzoic acid esters (e.g. methyl p-hydroxybenzoate, propyl p-hydroxy-benzoate, etc.); preservatives (e.g. benzyl alcohol, sorbic acid, etc.); antioxidants (e.g. butyl hydroxyanisol, sodium hydrogen sulfite, etc.); coloring agents (e.g. β-carotin, Food red No. 2, Food blue No. 1, etc.), etc. may be used.

The present invention is illustrated in more detail by the following Experiments and Examples, but should not be construed to be limited thereto.

EXPERIMENT 1

The Promotion Effects of a Combination of a Sucrose Fatty Acid Ester and an Organic Acid on Absorption of Calcitonin: Comparison with the Use of a Sucrose Fatty Acid Ester Alone and the Use of an Organic Acid Alone Human calcitonin (2 mg) was precisely measured, and thereto were added citric acid (50 mg) and a sucrose fatty acid ester (Ryoto-Sugar Ester S-970) (100 mg), and the mixture was well mixed. To the mixture was added a commercially available base for intravaginal preparation; Witepsol S-55 (which is prepared from Witepsol E-85 so as to give a final intravaginal suppository having a melting point of 36.5° C., manufactured by Hils Co., Ltd., former Diamit Novel Co., Ltd) which was homogenized by previously warming and stirring thereof so as to give an intravaginal suppository with the total weight of 5.00 g. The mixture was well mixed and distributed at about 40° C. by using a homogenizer to give a homogenous mixture for intravaginal suppository. The mixture was poured into a tube (inside diameter: about 3 mm) made of teflon at about 40° C., cooled to solidify, and taken out from the tube. The solidified mixture was cut into pieces (weight: 50 mg) to give intravaginal suppositories for rats containing human calcitonin (20 μg/each). There were also obtained two kinds of intravaginal suppositories prepared by adding citric acid (50 mg) only, and prepared by adding a sucrose fatty acid ester (100 mg) only, likewise. There were obtained intravaginal suppositories containing only human calcitonin without citric acid nor a sucrose fatty acid ester, likewise, which are used as control.

Ovariectomized female Wistar rats (weight: about 200–250 g) which had fasted overnight were anesthetized with ether, and the required amount of the blood was collected therefrom through the right external jugular vein prior to administration of a test preparation.

An intravaginal suppository was administered into the rat's vagina, and the blood was collected periodically (2, 4 and 6 hours after administration of the test preparation).

The serum was separated, and the calcium level in the serum was determined by using a kit for determination of calcium (Calcium C Test Wako; manufactured by Wako Pure Chemical Industries, Ltd.) (n=3).

The results are shown in Table 1.

As is clear from Table 1, by evaluating on the basis of the reduction rate of the calcium level in the serum, the calcitonin-absorption promotion effects were far superior in the case of administration of a combination of a sucrose fatty acid ester and citric acid in comparison with the case of administration of a sucrose fatty acid only or citric acid only.

TABLE 1

Reduction rate (%) of calcium level in the serum

| Intravaginal suppository | | Time after administration (hr) | | |
|---|---|---|---|---|
| Active Ingredient | Compounds to be added | 2 | 4 | 6 |
| Human calcitonin | Sucrose fatty acid ester (S-970) and citric acid | 14.9 | 19.5 | 11.1 |
| | Sucrose fatty acid ester (S-970) only | 10.6 | 10.5 | 10.7 |
| | Citric acid only | 9.5 | 8.0 | 5.7 |
| | Control | 2.6 | 2.2 | 3.8 |

EXPERIMENT 2

Effects of Various Bases on the Promotion Effects of a Combination of a Sucrose Fatty Acid Ester and an Organic Acid on Absorption of Calcitonin Human calcitonin (2 mg) was precisely measured, and thereto were added citric acid (50 mg) and Ryoto-Sugar Ester S-970 (100 mg), and the mixture was mixed well. To the mixture was added each one of the following bases (which was treated in the same manner as in Experiment 1 in order to adjust a melting point of the resulting suppositories) so as to give an intravaginal suppository with the total weight of 5.00 g. The mixture was well mixed and homogenized at about 40° C. by using a homogenizer to give a homogenous mixture for intravaginal suppository. The resultant was treated in the same manner as in Experiment 1 to give five kinds of intravaginal suppositories for rats weighing 50 mg per unit containing human calcitonin (20 μg).

In the same manner as in Experiment 1, each intravaginal suppository was administered to the rat's vagina, and the blood was collected periodically (2, 4 and 6 hours after administration of intravaginal suppository), and the calcium level in the serum thereof was determined (n=4).

Bases:
1. Witepsol H-15
2. Witepsol W-35
3. Witepsol S-55
4. Pharmasol B-105
5. Cacao butter
(Note: Pharmasol; manufactured by Nippon Fat and Oil Co., Ltd.)

The results are shown in Table 2.

As is seen from Table 2, a combination of a sucrose fatty acid ester and citric acid showed extremely excellent promotion effect on absorption of calcitonin regardless of any base to be used, and it is apparent that the effect thereof is not affected by any base to be used together.

TABLE 2

Reduction rate (%) of calcium level in the serum

| | | Time after administration (hr) | | |
|---|---|---|---|---|
| Active ingredient | Base to be used | 2 | 4 | 6 |
| Human calcitonin | Witepsol H-15 | 16.8 | 17.7 | 10.4 |
| | Witepsol W-35 | 6.6 | 20.4 | 13.2 |
| | Witepsol S-55 | 16.5 | 22.5 | 13.0 |
| | Pharmasol B-105 | 13.4 | 14.8 | 10.6 |
| | Cacao butter | 12.5 | 10.7 | 8.3 |

EXPERIMENT 3

Effects of Various Sucrose Fatty Acid Esters on the Promotion Effects of a Combination of a Sucrose Fatty Acid Ester and an Organic Acid on Absorption of Calcitonin Human calcitonin (2 mg) was precisely measured, and thereto were added citric acid (50 mg) and one of the following sucrose fatty acid esters (100 mg) having a different HLB value (Table A), and the mixture was well mixed. The resultant was treated in the same manner as in Experiment 1 to give six kinds of intravaginal suppositories for rats weighing 50 mg per unit containing human calcitonin (20 μg/each). In the same manner, there were prepared various sucrose fatty acid esters having the same HLB value but being combined with a different fatty acid (Table B), and four kinds of intravaginal suppositories for rats were prepared by using each 100 mg of sucrose fatty acid ester.

In the same manner as in Experiment 1, each intravaginal suppository was administered to the rat's vagina, and the blood was collected periodically (2, 4 and 6 hours after administration of intravaginal suppository), and the calcium level in the serum thereof was determined (n=4).

TABLE A

| Sucrose fatty acid ester | HLB value | Fatty acid to be combined |
|---|---|---|
| 1 Ryoto-Sugar Ester S-370 | 3 | Stearic acid |
| 2 Ryoto-Sugar Ester S-570 | 5 | Stearic acid |
| 3 Ryoto-Sugar Ester S-770 | 7 | Stearic acid |
| 4 Ryoto-Sugar Ester S-970 | 9 | Stearic acid |
| 5 Ryoto-Sugar Ester S-1670 | 16 | Stearic acid |
| 6 Ryoto-Sugar Ester L-1695 | 16 | Lauric acid |

TABLE B

| Sucrose fatty acid ester (HLB value: 9) | Combination ratio | Fatty acid to be combined |
|---|---|---|
| 1 Ryoto-Sugar Ester S-370 + S-1670 | (5:6) | Stearic acid |
| 2 Ryoto-Sugar Ester P-070 + P-1670 | (4:5) | Palmitic acid |
| 3 Ryoto-Sugar Ester L-595 + L-1695 | (3:2) | Lauric acid |
| 4 Ryoto-Sugar Ester S-970 | (Control) | Stearic acid |

The results are shown in Tables 3 and 4.

As is seen from Tables 3 and 4, the excellent promotion effects of a combination of a sucrose fatty acid ester and citric acid on absorption of calcitonin was not affected by either the HLB value of the sucrose fatty acid ester to be used or by the kinds of the fatty acids to be combined.

TABLE 3

Reduction rate (%) of calcium level in the serum

| Active ingredient | Sucrose fatty acid ester | HLB value | Fatty acid to be combined | Time after administration (hr) | | |
|---|---|---|---|---|---|---|
| | | | | 2 | 4 | 6 |
| Human calcitonin | Ryoto-Sugar Ester (S-370) | 3 | Stearic acid | 13.4 | 18.2 | 11.4 |
| | Ryoto-Sugar Ester (S-570) | 5 | Stearic acid | 12.8 | 17.2 | 12.0 |
| | Ryoto-Sugar Ester (S-770) | 7 | Stearic acid | 13.6 | 14.8 | 11.8 |
| | Ryoto-Sugar Ester (S-970) | 9 | Stearic acid | 12.2 | 17.4 | 11.8 |
| | Ryoto-Sugar Ester (S-1670) | 16 | Stearic acid | 11.4 | 16.4 | 12.6 |
| | Ryoto-Sugar Ester (L-1695) | 16 | Lauric acid | 12.8 | 13.4 | 11.4 |

TABLE 4

Reduction rate (%) of calcium level in the serum

| Active ingredient | Sucrose fatty acid ester Ryoto-Sugar Ester | Combination ratio | HLB value | Fatty acid to be combined | Time after administration (hr) | | |
|---|---|---|---|---|---|---|---|
| | | | | | 2 | 4 | 6 |
| Human calcitonin | S-370 + S-1670 | 5:6 | 9 | Stearic acid | 6.9 | 15.3 | 12.3 |
| | P-070 + P-1670 | 4:5 | 9 | Palmitic acid | 8.2 | 17.3 | 13.8 |
| | L-595 + L-1695 | 3:2 | 9 | Lauric acid | 11.0 | 14.4 | 9.7 |
| | S-970 | 1:0 | 9 | Stearic acid | 6.3 | 11.6 | 11.0 |

EXPERIMENT 4

Effects of the Concentration of Sucrose Fatty Acid Ester on the Promotion Effects on Absorption of Calcitonin Human calcitonin (2 mg) was precisely measured, and thereto were added citric acid (100 mg) and Ryoto-Sugar Ester S-970 (50 mg, 100 mg or 400 mg), and the mixture was mixed well. The resultant was treated in the same manner as in Experiment 1 to give three kinds of intravaginal suppositories for rats weighing 50 mg per unit containing human calcitonin (20 $\mu$g/each).

In the same manner as in Experiment 1, each intravaginal suppository was administered to the rat's vagina, and the blood was collected periodically (2 and 4 hours after administration of intravaginal suppository), and the calcium level in the serum thereof was determined (n=3).

The results are shown in Table 5.

As is clear from Table 5, by the promotion effect of a combination of a sucrose fatty acid ester and citric acid, the calcium level in the blood was reduced at any concentration of the sucrose fatty acid ester to be used.

TABLE 5

Reduction rate (%) of calcium level in the serum

| Active ingredient | Amount of sucrose fatty acid ester to be added (w/w % to the total weight of intravaginal suppository) | Time after administration (hr) | |
|---|---|---|---|
| | | 2 | 4 |
| Human calcitonin | 1 | 10.8 | 16.5 |
| | 2 | 8.0 | 18.2 |
| | 8 | 21.8 | 17.5 |

EXPERIMENT 5

The Promotion Effects of a Combination of a Sucrose Fatty Acid Ester and Various Organic Acids on Absorption of Calcitonin Human calcitonin (2 mg) was precisely measured, and dissolved in an aqueous solution of the following organic acid (50 mg) wherein the pH value was adjusted to pH 4, and thereto was added Ryoto-Sugar Ester R-970 (100 mg), and the mixture was mixed well. The resultant was treated in the same manner as in Experiment 1 to give four kinds of intravaginal suppositories for rats weighing 50 mg per unit containing human calcitonin (20 $\mu$g/each).

In the same manner as in Experiment 1, each intravaginal suppository was administered to the rat's vagina, and the blood was collected periodically (2, 4 and 6 hours after administration of intravaginal suppository), and the calcium level in the serum thereof was determined (n=5).

Organic acids:
1. Citric acid
2. Tartaric acid
3. Lactic acid
4. Malic acid

The results are shown in Table 6.

As is clear from Table 6, the calcium level was significantly reduced regardless of any organic acid to be used.

TABLE 6

Reduction rate (%) of calcium level in the serum

| Active ingredient | Organic acid to be used | Time after administration (hr) | | |
|---|---|---|---|---|
| | | 2 | 4 | 6 |
| Human calcitonin | Citric acid | 11.4 | 19.6 | 8.4 |
| | Tartaric acid | 12.2 | 8.0 | 3.4 |
| | Lactic acid | 17.0 | 10.6 | 5.4 |
| | Malic acid | 18.6 | 13.0 | 7.0 |

EXPERIMENT 6

Effects of the Concentration of Organic Acid on the Promotion Effects on Absorption of Calcitonin Human calcitonin (2 mg) was precisely measured, and dissolved in an aqueous solution (700 mg) containing citric acid (50 mg), an aqueous solution (750 mg) containing citric acid (100 mg), an aqueous solution (900 mg) containing citric acid (250 mg), or an aqueous solution (1150 mg) containing citric acid (500 mg), wherein the pH value was adjusted to pH 3.5, and thereto was added Ryoto-Sugar Ester S-970 (100 mg), and the mixture was well mixed and homogenized. Each resultant was treated in the same manner as in Experiment 1 to give four kinds of intravaginal suppositories for rats weighing 50 mg per unit containing human calcitonin (20 µg/each).

In the same manner as in Experiment 1, each intravaginal suppository was administered to the rat's vagina, and the blood was collected periodically (2, 4 and 6 hours after administration of intravaginal suppository), and the calcium level in the serum thereof was determined (n=3).

The results are shown in Table 7.

As is clear from Table 7, by the promotion effect of a combination of a sucrose fatty acid ester and citric acid, the calcium level in the blood was reduced at any concentration of citric acid to be used.

TABLE 7

Reduction rate (%) of calcium level in the serum

| Active ingredient | Amount of organic acid to be added (w/w % to the total weight of intravaginal suppository) | Time after administration (hr) | | |
|---|---|---|---|---|
| | | 2 | 4 | 6 |
| Human calcitonin | 1 | 14.6 | 15.7 | 9.2 |
| | 2 | 15.3 | 18.7 | 8.2 |
| | 5 | 17.9 | 19.4 | 7.5 |
| | 10 | 18.4 | 19.0 | 5.0 |

EXPERIMENT 7

Effects of pH Value of the Solution in an Intravaginal Suppository on the Promotion Effect on Absorption of Calcitonin Human calcitonin (2 mg) was precisely measured, and dissolved in an aqueous solution containing citric acid (100 mg), wherein the pH value was adjusted to pH 3.0, pH 3.5, pH 4.0, pH 4.5, pH 5.0 or pH 5.5, and thereto was added Ryoto-Sugar Ester S-970 (100 mg), and the mixture was well mixed and homogenized. Each resultant was treated in the same manner as in Experiment 1 to give six kinds of intravaginal suppositories for rats weighing 50 mg per unit containing human calcitonin (20 µg/each).

In the same manner as in Experiment 1, each intravaginal suppository was administered to the rat's vagina, and the blood was collected periodically (2, 4 and 6 hours after administration of intravaginal suppository), and the calcium level in the serum thereof was determined (n=3).

The results are shown in Table 8.

As is clear from the results, the promotion effect of a combination of a sucrose fatty acid ester and citric acid was observed in the cases of pH 3.0 to 5.5, and the effects thereof were not significantly different in the cases of pH 3.0 to 4.5.

TABLE 8

Reduction rate (%) of calcium level in the serum

| pH of the solution in intravaginal suppository | Time after administration (hr) | | |
|---|---|---|---|
| | 2 | 4 | 6 |
| 3.0 | 11.0 | 22.0 | 8.7 |
| 3.5 | 9.4 | 19.8 | 8.8 |
| 4.0 | 9.4 | 20.2 | 10.2 |
| 4.5 | 9.5 | 22.8 | 9.1 |
| 5.0 | 10.2 | 11.4 | 2.7 |
| 5.5 | 8.1 | 13.2 | 4.3 |

EXPERIMENT 8

Administration Test of Calcitonin Intravaginal Suppository on Beagles; Cross Over Test Elcatonin (4 mg) was precisely measured, and dissolved in an aqueous solution (2.5 g) containing citric acid (0.5 g) wherein the pH value was adjusted to pH 3.2, and to the mixture was added Ryoto-Sugar Ester S-970 (1.0 g), and the mixture was mixed well.

To the mixture was added Witepsol S-55 which was previously homogenized by warming and stirring (a melting point thereof was adjusted in the same manner as in Experiment 1) so that the total weight of the resulting intravaginal suppositories was 50.0 g. The mixture was well homogenized at about 40° C. by using a homogenizer to give a homogenous mixture for intravaginal suppositories. The mixture was poured into a commercially available plastic container for suppositories (0.9 ml, manufactured by KANAE, Ltd.) to give suppositories (about 0.5 g each). After cooling to solidify, intravaginal suppositories for beagles containing elcatonin (40 µg per unit) were obtained.

Ovariectomized female beagles (weight: about 10–12 kg) which had fasted overnight were used. The required amount of the blood was collected therefrom through the antebrachial vein prior to administration of a test preparation.

The above mentioned ovariectomized beagles were divided out into two groups (three animals/group). The above intravaginal suppository was administered into the vagina of the animals in one group, and to the animals in the other group, an injection containing elcatonin (8 µg/ml) (Elcitonin, manufactured by Asahi Kasei Kogyo Kabushiki Kaisha) was administered intramuscularly, and the blood was collected periodically (10, 20, 30, 45, 60, 90, 120, 180 and 240 minutes after administration). After the plasma was separated, the elcatonin level in the plasma was determined by RIA method (radio immunoassay: by competitive method using $^{125}$I-elcatonin). Subsequently, the administration routes of these two groups were exchanged, i.e. intramuscular administration to the first group, and intravaginal administration to the second group, and the elcatonin level in the plasma in each group was determined likewise.

The results are shown in Table 9.

As is clear from Table 9, when the change in the elcatonin level in the plasma was compared, the elcatonin level in the plasma in case of administration of intravaginal suppository containing a combination of a sucrose fatty acid ester and citric acid was changed in the same pattern as that of in case of intramuscular administration. Thus, when administered by the intravaginal preparation of the present invention, the same pharmacological effect as that of intramuscular administration was obtained at a dose of about five times larger than that of intramuscular administration, which is extremely excellent.

TABLE 9

Elcatonin level in the plasma (pg/ml)

| Administration site | Preparation form | Dose of elcatonin | Time after administration (min) | | | | | | | | |
|---|---|---|---|---|---|---|---|---|---|---|---|
| | | | 10 | 20 | 30 | 45 | 60 | 90 | 120 | 180 | 240 |
| Intramuscular | Injection | 8 μg | 315 | 368 | 337 | 255 | 165 | 82 | 50 | 16 | −4 |
| Vagina | Intravaginal suppository | 40 μg | 158 | 363 | 370 | 363 | 231 | 128 | 76 | 36 | −10 |

EXPERIMENT 9

Administration Test of (1-34)-Teriparatide Acetate (PTH) Intravaginal Suppository on Rats (1-34)-Teriparatide acetate (2 mg, manufactured by Asahi Kasei Kogyo Kabushiki Kaisha) was precisely measured, and thereto were added citric acid (50 mg) and Ryoto-Sugar Ester S-970 (100 mg). The mixture was well mixed and homogenized. The resulting mixture was treated in the same manner as in Experiment 1 to give intravaginal suppositories for rats weighing 50 mg per unit containing teriparatide acetate (4 μg/each).

Ovariectomized female Wistar rats (weight: about 200–250 g) which had fasted overnight were anesthetized with ether, and the required amount of the blood was collected therefrom through the right external jugular vein prior to administration of a test preparation.

The above ovariectomized rats were divided out into two groups (three animals/group). The above intravaginal suppository was administered into the vagina of the animals in one group, and to the animals in the other group, an injection (0.2 ml) containing PTH (3 μg/ml) which was prepared by dissolving teriparatide acetate in sterile physiological saline solution (1 ml) was administered intramuscularly. The blood was collected periodically (30, 60, 120 and 240 minutes after administration), and the PTH level in the plasma was determined by using a kit for determination of PTH (INS-PTH Kit, manufactured by Ecolsu Co., Ltd.).

The results are shown in Table 10.

As is clear from Table 10, when the change in the PTH level in the plasma was compared, the PTH level in the plasma in case of administration of intravaginal suppository containing a combination of a sucrose fatty acid ester and an organic acid at a dose of about 6 times larger than that of intramuscular administration was changed in the same pattern as that of in case of intramuscular injection administration, which is the same as in the case of elcatonin in Experiment 8.

TABLE 10

PTH level in the plasma (pg/ml)

| Administration site | Preparation form | Dose of PTH | Time after administration (hr) | | | |
|---|---|---|---|---|---|---|
| | | | 30 | 60 | 120 | 240 |
| Intramuscular | Injection | 0.6 μg | 530 | 298 | 136 | 21 |
| Vagina | Intravaginal suppository | 4.0 μg | 575 | 437 | 170 | 87 |

EXAMPLE 1

Preparation of Intravaginal Suppositories

A conventional base for suppository such as Witepsol, macrogol, glycerogelatin can be used for preparation of suppositories. A liquid or a paste-like mixture containing a physiologically active peptide is well mixed with a base for suppository at an appropriate temperature (i.e. at a lowest temperature being sufficient to give a suitable fluidity to a base for suppository) by using a mechanical mixing apparatus (e.g. homogenizer, mixer, etc.) to give a homogenized mixture. The mixture is poured into a mold for suppository, and cooled.

In the following formulations, intravaginal suppositories are prepared according to the method of Experiment 5, wherein a plastic container for suppository (0.9 ml) was used as a mold. In the following each formulation, Ryoto-Sugar Ester S-970, which is a representative of sucrose fatty acid ester, is used as a sucrose fatty acid ester, and Witepsol S-55, a representative of Witepsol, is used as a base for suppository, but other examples therefor as mentioned above can be used not only in this example but also in the other Examples.

Formulation 1

| Elcatonin | 0.004 g |
| Citric acid | 0.5 g |
| Sodium hydroxide solution | 2.0 g |
| Sucrose fatty acid ester | 1.0 g |
| Witepsol | q.s. |
| Totally | 50.0 g (for 100 suppositories) |

Formulation 2

| Human calcitonin | 0.002 g |
| Succinic acid | 0.05 g |
| Sodium hydroxide solution | 0.6 g |
| Sucrose fatty acid ester | 0.1 g |
| Bovine serum albumin (BSA) | 0.015 g |
| Butyl p-hydrooxybenzoate | 0.001 g |
| Witepsol | q.s. |
| Totally | 5.0 g (for 10 suppositories) |

In the following formulations, intravaginal suppositories are prepared according to the method of Experiment 1, wherein a plastic container for suppository (0.9 ml) is used as a mold, like in Example 1.

Formulation 1

| Human calcitonin | 0.002 g |
| Phthalic acid | 0.05 g |
| Sucrose fatty acid ester | 0.1 g |
| Witepsol | q.s. |
| Totally | 5.0 g (for 10 suppositories) |

Formulation 2

| Salmon calcitonin | 0.002 g |
| Fumaric acid | 0.5 g |
| Sucrose fatty acid ester | 0.1 g |
| Witepsol | q.s. |
| Totally | 50.0 g (for 100 suppositories) |

| Formulation 3 | |
|---|---|
| Insulin | 1,000 I.U. |
| p-Hydroxybenzoic acid | 0.05 g |
| Sucrose fatty acid ester | 0.1 g |
| Witepsol | q.s. |
| Totally | 5.0 g (for 10 suppositories) |

EXAMPLE 2

Preparation of Intravaginal Tablets

In preparation of tablets, a liquid or a paste-like mixture containing a physiologically active peptide is mixed well with a suitable additive such as fillers, binders, disintegrators, etc., and the mixture is dried, and if necessary, thereto are added other additives such as lubricants. The final mixture is tabletted with a pounder to give tablets.

In preparation of non-disintegration tablets, it is necessary to use a base being able to produce a hydrogel in the vagina for the intravaginal preparation of the present invention. The base includes, for example, glucomannan, alginic acid, a calcium salt thereof, pectin, hydroxypropylmethyl cellulose, etc. The pharmacological action of the active ingredient is exhibited quickly in disintegration tablets, but the non-disintegration tablets usually show sustained release properties.

In the following formulations, intravaginal tablets are prepared in a conventional manner.

| Formulation 1 | |
|---|---|
| Elcatonin | 0.004 g |
| Valeric acid | 0.5 g |
| Sodium hydroxide solution | 2.0 g |
| Sucrose fatty acid ester | 1.0 g |
| CMC · Na | 1.0 g |
| Corn starch | 15.0 g |
| Lactose | q.s. |
| Totally | 50.0 g (for 100 tablets) |
| Formulation 2 | |
| Human PTH | 0.002 g |
| Ascorbic acid | 0.05 g |
| Sodium hydroxide solution | 0.2 g |
| Sucrose fatty acid ester | 0.1 g |
| CMC · Na | 0.1 g |
| Corn starch | 1.5 g |
| Lactose | q.s. |
| Totally | 5.0 g (for 10 tablets) |

EXAMPLE 3

Preparation of Intravaginal Foaming Tablets

In preparation of the intravaginal tablets in Example 2, a carbonate such as sodium hydrogen carbonate is used as an additive, and the amount of an organic acid is considerably increased to give intravaginal foaming tablets.

In the following formulations, intravaginal foaming tablets are prepared in a conventional manner.

| Formulation 1 | |
|---|---|
| Human calcitonin | 0.004 g |
| Propionic acid | 0.05 g |
| Sodium hydroxide solution | 0.2 g |
| Sucrose fatty acid ester | 0.1 g |
| Citric acid | 0.5 g |
| CMC · Na | 0.1 g |
| Corn starch | 1.0 g |
| Sodium hydrogen carbonate | 0.5 g |
| Magnesium stearate | 0.25 g |
| Lactose | q.s. |
| Totally | 5.0 g (for 10 tablets) |
| Formulation 2 | |
| Insulin | 1,000 I.U. |
| Lactic acid | 0.05 g |
| Sucrose fatty acid ester | 0.1 g |
| Citric acid | 0.5 g |
| CMC · Na | 0.1 g |
| Corn starch | 1.0 g |
| Sodium hydrogen carbonate | 0.5 g |
| Magnesium stearate | 0.25 g |
| Lactose | q.s. |
| Totally | 5.0 g (for 10 tablets) |

EXAMPLE 4

Preparation of Intravaginal Cream

In preparation of creams, both oil in water cream and water in oil cream can be prepared according to the formulation of the present invention.

In the following formulations, intravaginal cream is prepared in a conventional manner.

| Formulation 3 | |
|---|---|
| Insulin | 1,000 I.U. |
| Fumaric acid | 0.05 g |
| Sodium hydroxide solution | 0.2 g |
| Sucrose fatty acid ester | 0.1 g |
| White petrolatum | 1.25 g |
| Stearyl alcohol | 1.0 g |
| PG | 0.5 g |
| Glycerin monostearate | 0.25 g |
| Methyl p-hydroxybenzoate | 0.005 g |
| Purified water | q.s. |
| Totally | 5.0 g (for 10 units) |
| Formulation 2 | |
| Elcatonin | 0.004 g |
| Tartaric acid | 0.5 g |
| Sodium hydroxide solution | 2.0 g |
| Sucrose fatty acid ester | 1.0 g |
| White petrolatum | 12.5 g |
| Stearyl alcohol | 10.0 g |
| PG | 5.0 g |
| Glycerin monostearate | 2.5 g |
| Methyl p-hydroxybenzoate | 0.05 g |
| BSA | 0.15 g |
| Purified water | q.s. |
| Totally | 50.0 g (for 100 units) |

Other intravaginal preparations of the present invention are prepared in the following manner.

A film preparation is prepared by mixing and stirring the above liquid or paste-like mixture with a base for film such as hydropropylmethyl cellulose, chitosan, pullulan, glucomannan, polyacrylate ester, etc., to give a homogenous mixture, and being further subjected to casting and distilled (dried).

A soft capsule is prepared by sealing an oily or polyethylene glycol mixture containing a physiologically active peptide into soft capsules.

Tampon preparation can be prepared by various methods. For example, a tampon-shape core made of silicon resin is coated with a polymer film such as chitosan, polyacrylate methacrylate copolymer, containing a physiologically active peptide.

EFFECTS OF INVENTION

When a physiologically active peptide is administered orally, it is hydrolyzed by a protease, and cannot be absorbed enough. As a result, said physiologically active peptide cannot exhibit the desired pharmacological activity thereof. Thus, these peptides are usually administered in injection form. By the present intravaginal preparation which comprises at least a combination of an organic acid and a sucrose fatty acid ester, a hardly-absorbable peptide is well absorbed even at a small dose by addition of a small amount of a sucrose fatty acid ester and an organic acid. Accordingly, when the intravaginal preparation of the present invention is used, the same pharmacological effects as those which are obtained by an injection preparation can easily be obtained with less pain. Especially, in the treatment of chronic diseases which require frequent administration of medicaments, the intravaginal preparation of the present invention can easily be administered to the patients by themselves, which makes it possible to treat the patients at home.

As mentioned above, the intravaginal preparations of the present invention are very important by which the disadvantages of the conventional injections may be overcome.

We claim:

1. A method of administering a preparation containing a physiologically active peptide to a patient in need thereof, wherein the preparation comprises a physiologically active peptide, a sucrose fatty acid ester and an organic acid which is selected from the group consisting of malic acid, lactic acid and citric acid, or a pharmaceutically acceptable salt thereof in a pharmaceutically acceptable carrier or diluent, and which preparation has a pH value of 3 to 7; said method comprising administering the preparation to the patient intravaginally.

2. The method according to claim 1, wherein the organic acid is citric acid.

* * * * *

UNITED STATES PATENT AND TRADEMARK OFFICE
CERTIFICATE OF CORRECTION

PATENT NO. : 6,008,189
DATED : December 28, 1999
INVENTOR(S) : Inamoto et al.

It is certified that error appears in the above-identified patent and that said Letters Patent is hereby corrected as shown below:

Title Page,
In category "[62] Related U.S. Application Data", please change "Division of application No. 08/557,104, filed as application No. PCT/JP94/00894, June 2, 1994" to -- Division of application No.08/557,104, filed December 6, 1995, which was the national stage of international application number PCT/JP94/00894, filed June 2, 1994--

Signed and Sealed this

Third Day of July, 2001

*Attest:*

*Attesting Officer*

NICHOLAS P. GODICI
*Acting Director of the United States Patent and Trademark Office*